United States Patent [19]
Wong

[11] Patent Number: 5,498,255
[45] Date of Patent: Mar. 12, 1996

[54] OSMOTIC DEVICE FOR PROTRACTED PULSATILE DELIVERY OF AGENT

[75] Inventor: Patrick S.-L. Wong, Palo Alto, Calif.

[73] Assignee: ALZA Corporation, Palo Alto, Calif.

[21] Appl. No.: 442,716

[22] Filed: May 15, 1995

Related U.S. Application Data

[63] Continuation of Ser. No. 108,094, Aug. 17, 1993, abandoned.

[51] Int. Cl.$^6$ ........................................ A61K 9/22
[52] U.S. Cl. ............... 604/892.1; 424/453; 424/472; 424/473
[58] Field of Search ............... 604/892.1, 890.1, 604/891.1; 424/453, 468, 471, 472, 474, 462, 463, 48, 473, 422–424

[56] References Cited

U.S. PATENT DOCUMENTS

| | | | |
|---|---|---|---|
| 3,732,865 | 5/1973 | Higuchi et al. | 424/453 X |
| 3,845,770 | 11/1974 | Theeuwes et al. | |
| 3,865,108 | 2/1975 | Hartop | |
| 3,944,064 | 3/1976 | Bashaw et al. | 424/422 X |
| 3,995,631 | 12/1976 | Higuchi et al. | |
| 4,002,173 | 1/1977 | Manning et al. | |
| 4,034,756 | 7/1977 | Higuchi et al. | |
| 4,111,202 | 9/1978 | Theeuwes | |
| 4,207,893 | 6/1980 | Michaels | |
| 4,265,874 | 5/1981 | Bonsen et al. | |
| 4,320,759 | 3/1982 | Theeuwes | |
| 4,327,725 | 5/1982 | Cortese et al. | |
| 4,449,983 | 5/1984 | Cortese et al. | |
| 4,595,583 | 6/1986 | Eckenhoff et al. | |
| 4,612,008 | 9/1986 | Wong et al. | |
| 4,874,388 | 10/1989 | Wong et al. | 604/891.1 |
| 4,994,273 | 2/1991 | Zentner et al. | 424/422 |
| 5,308,348 | 5/1994 | Balaban et al. | 604/892.1 |
| 5,387,421 | 2/1995 | Amidon et al. | 424/472 |
| 5,391,381 | 2/1995 | Wong et al. | 424/473 |
| 5,415,868 | 5/1995 | Smith et al. | 424/454 |

FOREIGN PATENT DOCUMENTS

| | | |
|---|---|---|
| WO90/09169 | 8/1990 | WIPO. |
| WO92/13521 | 8/1992 | WIPO. |

*Primary Examiner*—C. Fred Rosenbaum
*Assistant Examiner*—V. Alexander
*Attorney, Agent, or Firm*—Felissa H. Cagan; Steve F. Stone; Edward L. Mandell

[57] ABSTRACT

The present invention is directed to a fluid-imbibing dispensing device for the extended or protracted delivery of an active agent following an initially delayed startup of the delivery to a fluid environment of use. The dispenser comprises a housing having a first wall section and a second wall section in reversibly sliding telescopic arrangement with each other, which housing maintains its integrity in the environment of use; an internal compartment surrounded and defined by the housing; at least one active agent formulation in a portion of the compartment defined by the first wall section; at least one opening in the side wall of the first wall section, each opening extending longitudinally along a portion of the side wall of the first wall section for providing communication between the active agent formulation and the environment; expansion means within a portion of the compartment defined by the second wall section, for separating apart the first and second wall sections of the housing after exposure to the environment of use; and, optionally, a partition layer or push plate between the active agent formulation and the expansion means.

10 Claims, 1 Drawing Sheet

OSMOTIC DEVICE FOR PROTRACTED PULSATILE DELIVERY OF AGENT

This application is a continuation of application Ser. No. 08/108,094, filed Aug. 17, 1993, now abandoned and benefit of the filing date of said earlier filed application is claimed under 35 U.S.C. § 120.

FIELD OF THE INVENTION

The present invention is related to the protracted pulsatile delivery of an active agent. More particularly, it is related to osmotically-activated devices for dispensing active agents to a biological environment of use for an extended or protracted period of time following an initial delay.

BACKGROUND OF THE INVENTION

Osmotic dispensing devices for delivery of therapeutically active agents are well known in the art. Such devices use an expansion means to deliver an agent to an environment of use over a period of hours, days or months. The expansion means absorbs liquid, expands, and acts to drive out beneficial agent formulation from the interior of the device in a controlled, usually constant manner. The osmotic expansion means is used to controllably, usually relatively slowly, and over a period of time, deliver the agent. Thus, these devices are not generally used to delay the initial release of the agent.

The delay of the initial release of an agent has primarily been previously effected by coating the agent or a formulation containing the agent with a dissolvable or bioerodible coating layer, such as gelatin, which coating dissolves or erodes in the environment of use to then make the agent available. Delayed initial release has also been provided by dispersing the agent in a dissolvable or erodible matrix. However, such systems are often unreliable and release cannot be controlled with great accuracy due to the variability and relatively uncontrollable nature of erosion and dissolution.

Therefore, there remains a continuing need for improved methods and systems for providing a delayed initial delivery of an active agent to an environment of use that are reliable and that can be programmed to deliver the agent after a particular interval with increased accuracy. In addition, there is a need for systems which provide a protracted pulse delivery of an agent following a delayed startup, which delivery, once begun, can be extended and otherwise controlled.

SUMMARY OF THE INVENTION

The present invention is directed to a fluid-imbibing dispensing device for the extended or protracted delivery of an active agent following an initially delayed startup of the delivery to a fluid environment of use. The dispenser comprises a housing having a first wall section and a second wall section in reversibly sliding telescopic arrangement with each other, which housing maintains its integrity in the environment of use; an internal compartment surrounded and defined by the housing; at least one active agent formulation in a portion of the compartment defined by the first wall section; at least one opening in the side wall of the first wall section, each opening extending longitudinally along a portion of the side wall of the first wall section, for providing communication between the active agent formulation and the environment; expansion means within a portion of the compartment defined by the second wall section, for separating apart the first and second wall sections of the housing after exposure to the environment of use; and, optionally, a partition layer or push plate between the active agent formulation and the expansion means.

The invention also is directed to a method for delaying the initial delivery of an active agent to a fluid environment of use, after which delay the active agent is delivered to the environment over an extended period and in a protracted manner, the method comprising placing the dispensing device of the invention into the environment of use, allowing fluid to be imbibed through at least a portion of the housing of the dispensing device for causing the expansion means to expand and exert pressure on the slidably connected first and second wall sections to push apart and separate the two wall sections to deliver an active agent formulation through the opening or plurality of openings in the first wall section to the environment after an initially delayed period of time. That is, as the two wall sections are being pushed apart, an increasing area of the opening or openings becomes exposed to the fluid environment, allowing the active agent formulation to leach out of the device through the openings to provide a protracted pulse of agent delivery.

During the initial delay period in the environment, the volume of that portion of the compartment containing the active agent is kept constant; therefore, there is a negligible pressure gradient between the environment and the interior of the agent-containing compartment. As a result, net flow of the environmental fluid driven by the pressure to enter the agent-containing compartment is minimal, so that the active agent is not contaminated or diluted prior to commencement of delivery.

DESCRIPTION OF THE DRAWINGS

The drawings are not drawn to scale, but are set forth to illustrate various embodiments of the invention. Like numbers refer to like structures.

DETAILED DESCRIPTION OF THE INVENTION

The present invention provides a device which is useful for the initial delayed delivery of an active agent formulation to a fluid environment of use, the delivery of the agent formulation from the dispensing device, once begun, being continued over an extended period; that is, all of the agent is not released into the environment at one time. By "extended period of time" is meant a protracted time period such as for one hour, up to several hours, days, weeks or months.

As used herein, the terms "therapeutically effective" amount or rate refer to the amount or rate of the active agent needed to effect the desired therapeutic, often beneficial, result.

The dispensing devices of the invention find use, for example, in humans or other animals. The environment of use is a fluid environment and can comprise the stomach, the intestinal tract, or a body cavity such as the peritoneum or vagina. A single dispensing device or several dispensing devices can be administered to a subject during a therapeutic program.

Figure 1:
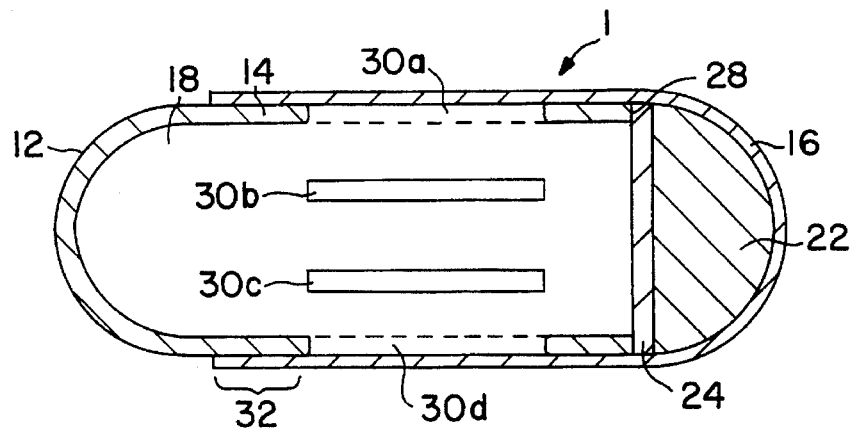
FIG. 1 is a cross-sectional view of one embodiment of the present invention, the device being in closed or prepared form prior to placement in the environment of use.

FIG. 1 depicts in cross-sectional view a presently preferred embodiment of the delivery device according to the present invention. The device is shown in closed or prepared form prior to placement in the environment of use. Dispensing device 1 comprises a housing 12 formed of a first wall section 14 and a second wall section 16. First wall section 14 and second wall section 16 are in reversibly sliding telescopic arrangement with each other. Housing 12 surrounds and defines an internal compartment 18. First wall section 14 surrounds that portion of internal compartment 18 that contains an active agent formulation 20 (not shown in FIG. 1). Second wall section 16 surrounds that portion of internal compartment 18 that contains an expansion means 22 for expanding and for occupying space in compartment 18. Second wall section 16 also contains a partition layer or push plate 24, which push plate 24 is positioned between the agent formulation 20 and the expansion means 22. Push plate 24, in a presently preferred embodiment, comprises a composition that is substantially impermeable to the passage of fluid, and it serves to restrict the passage of fluid present in the expansion means into that area of compartment 18 that contains the agent formulation. It operates to essentially maintain the integrity of the active agent formulation and the expansion means layer. Additionally, and importantly, push plate 24 acts to insure that the expanding driving force generated by the expansion means 22 is applied directly against the first wall section 14 to effect the separation of the two wall sections. Thus, push plate 24 must be of sufficient strength, thickness and rigidity to transfer the driving force against first wall section 14.

Each of first wall section 14 and second wall section 16 has an open end, the open end of first wall section 14 being adapted to fit within the open end of second wall section 16. The two wall sections at their open ends are close in size and they form a friction fit therebetween. The friction generated is sufficient to maintain the two wall sections together prior to activation of the expansion means but not so great as to keep the two wall sections from sliding apart once an expanding driving force is exerted. Where additional friction is desired, protrusions may be present at or near the open end of the first wall section for providing further friction between the two wall sections. First wall section 14 and second wall section 16 can be telescoped completely into a closed external walled position. The bottom edge of the open end of first wall section 14 provides a platform or ridge 28 protruding into compartment 18. Ridge 28 is adapted to receive the driving force of the expansion means 22, via the push plate 24, to effect the separation of the two wall sections.

First wall section 14 has a plurality of openings 30, shown in device 1 as four elongated openings 30a, 30b, 30c and 30d, which extend longitudinally along a portion of the side wall of the first wall section. According to the invention, the number of openings is variable, and may be selected from, generally, one to ten openings, or more, to moderate the rate of leaching of agent from the device. In a presently preferred embodiment, the number of openings 30 is from two to ten, depending on the protraction of release that is desired. The openings can have any shape, but in a preferred embodiment the shape is an elongated rectangle or ellipse. Alternatively, each opening 30 may consist of a series of smaller openings, such as for example squares, circles, triangles, rectangles or ellipses, extending longitudinally along the side wall of the first wall section 14.

In operation, as the expansion means 22 absorbs and imbibes fluid through second wall section 16 from the environment of use, it expands and pushes against push plate 24, causing the push plate to slide inside compartment 18. Push plate 24 moves toward and contacts ridge 28, pushing against ridge 28 and thus against first wall section 14 to cause the first wall section to slide apart from second wall section 16 as the expansion means 22 continues to expand. As the two wall sections are pushed apart, the openings 30 begin to become progressively exposed to the environment, causing the active agent formulation 20 to be exposed and released to the environment of use via the exposed portions of the openings 30, as illustrated in FIGS. 2 and 3.

Figure 2:
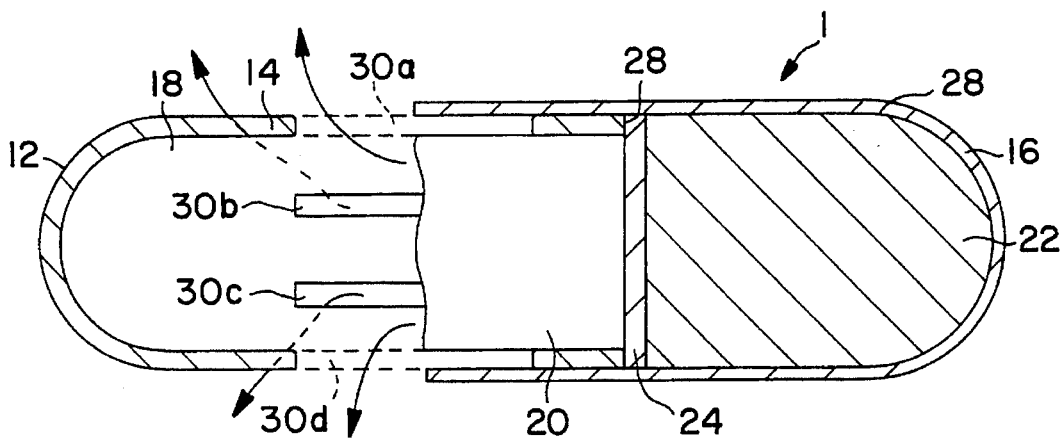
FIG. 2 is the device of FIG. 1 in operation after activation by placement in the environment of use, showing the device partially opened to release the active agent formulation to the environment.
Figure 3:
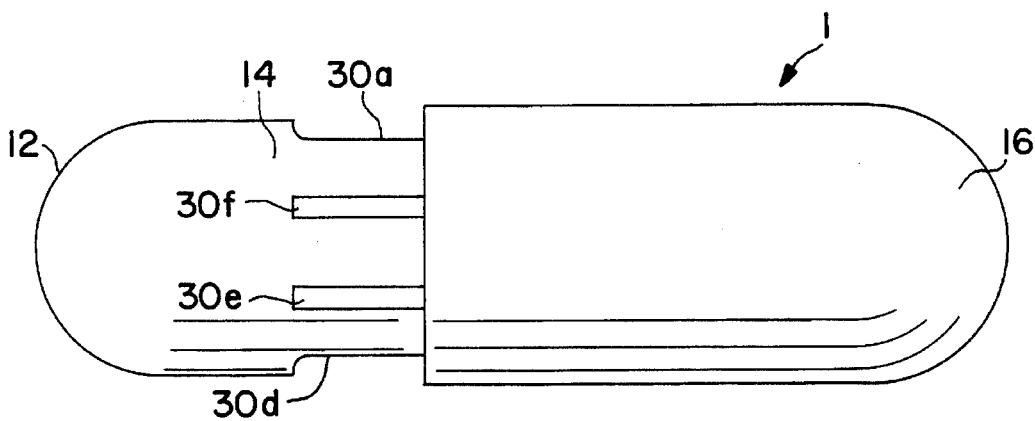
FIG. 3 is an exterior side view of the device of FIG. 2.

FIGS. 2 and 3 illustrate the dispensing device 1 of FIG. 1 in operation after activation of the device by placement in the environment of use. FIGS. 2 and 3 show device 1 partially opened to release a portion of the active agent formulation 20 to the environment (FIG. 2 as a longitudinal cross-sectional view and FIG. 3 as a longitudinal exterior view). As illustrated in FIG. 2, first wall section 14 has been partially separated from second wall section 16 to expose a portion of the openings 30, separation having occurred by the expanding driving force of the expansion means 22, which has expanded in size as a result of imbibing fluid from the environment. The arrows in FIG. 2 indicate the exiting of the active agent formulation 20 from internal compartment 18 through the exposed portions of the openings 30 in first wall section 14, which are now in communication with the environment.

The delivery profile of the active agent from the device of the present invention can be determined by varying the characteristics of the openings 30, such as by varying the number, size and/or placement of the openings. For example, the time period for the initial delay of startup of delivery can be set by the initial distance of the openings from the open end of the second wall section 16, the initial distance illustrated as distance 32 in FIG. 1. The amount of active agent released over time can be determined by the length of the openings, by the number of openings present in the wall, by the width of the openings, or by a combination of these.

First wall section 14 may comprise a composition that is semipermeable, that is, it is permeable to fluid but impermeable to active agent and other ingredients contained in dispensing device 1, or it may, alternatively, comprise a composition that is impermeable to the exchange of fluid, agent and other ingredients. When an active agent or an active agent dosage form is sensitive to fluid from an exterior fluid present in the environment of use, it is preferred that first wall section 14 be substantially impermeable to the ingress of the external fluid to serve as a means for substantially protecting the agent or dosage form.

Because expansion means 22 operates by the imbibition of external fluid, second wall section 16 in at least a portion that is initially adjacent to expansion means 22 must be semipermeable; that is, it is permeable to the passage of fluid while being substantially impermeable to the passage of other ingredients contained in dispensing device 1. In one embodiment, second wall section 16 is semipermeable in its entirety. In another embodiment, second wall section 16 is composed of an impermeable material in that portion that initially contacts the openings 30, in order to protect the active agent from exposure to fluid from the fluid environment until such time as openings 30 themselves are exposed to the environment.

Wall sections 14 and 16 optionally comprise additional ingredients such as, for example, a plasticizer. Impermeable and semipermeable compositions suitable for use in wall sections 14 or 16, as well as suitable additives, are known in the art, examples of which are disclosed in U.S. Pat. No. 4,874,388, the entire disclosure of which is incorporated herein by reference.

Housing 12, comprising wall sections 14 and 16, is nontoxic, biologically inert, nonallergenic and nonirritating to body tissue, and it maintains its physical and chemical integrity; that is, housing 12 does not erode or degrade in the environment of use during the dispensing period. It is within the scope of the invention that the housing be insoluble only during the period of intended use and can thereafter dissolve away in the environment of the device. Thus, a dispenser is here contemplated which is unaffected by its environment, solubility-wise, at the situs of use or which, alternatively, is only slightly soluble during the period of intended use, such that once its active agent content has been removed it will then dissolve or erode away leaving no objectionable residue or empty container at the situs of use.

The expansion means or expandable driving means 22, operable for separating the first and second wall sections to release the active agent from the dispensing device of the invention, is nontoxic, nonallergenic and biologically inert. Expansion means 22 comprises, in one presently preferred embodiment, an osmopolymer. The osmopolymers interact with water and aqueous biological fluids and swell or expand to an equilibrium state. The osmopolymers exhibit the ability to swell in fluid and to retain a significant portion of the imbibed and absorbed fluid within the polymer structure. The expansion means 22 in another preferred embodiment comprises an osmagent. The osmagents are known also as osmotically effective solutes and they are also known as osmotically effective compounds. The osmagents that can be used for the purpose of this invention include inorganic and organic compounds that exhibit an osmotic pressure gradient across a semipermeable, i.e. a fluid-permeable, wall. The expansion means 22 in yet another preferred embodiment comprises an osmagent dispersed within an osmopolymer. The expansion means 22 can comprise a tablet or a layer, or a plurality of tablets or layers, or it can be pressed into second wall section 16. The osmagent or osmopolymer can be in any suitable form such as particles, crystals, pellets, granules, and the like, when pressed into a tablet layer and into wall section 16. Osmagents and osmopolymers are known to the art and are described in, for example, U.S. Pat. Nos. 3,865,108, 4,002,173, 4,207,893, 4,327,725 and 4,612,008.

Push plate 24, present in certain embodiments of the invention between the active agent formulation and the expansion means, is a means for transmitting the force generated by the expansion means against the first wall section 14, for maintaining the separate identity of the active agent formulation and the expansion means, and for substantially restricting the passage of fluid between the active agent formulation and the expansion means. Representative materials useful as a partition layer or push plate 24 are known to the art in, for example, U.S. Pat. No. 4,874,388.

The term "active agent formulation", as used herein, comprises the active agent to be delivered, as a liquid, solid, semisolid or thermosensitive composition, generally in a carrier substance and with or without additional inert ingredients. The term may additionally include dosage forms comprising the active agent which are capable of maintaining their physical configuration and chemical integrity while housed within the dispenser. These include, without limitation, tablets with or without a density element; matrix tablets; spheres; tiny pills; pellets and elongated tablets; capsules; elementary osmotic pumps, such as those described in U.S. Pat. No. 3,845,770; miniosmotic pumps, such as those described in U.S. Pat. Nos. 3,995,631, 4,034,756 and 4,111,202; and multichamber osmotic systems referred to as push-pull and push-melt osmotic pumps, such as those described in U.S. Pat. Nos. 4,320,759 and 4,449,983; all the above patents of which are incorporated herein by reference.

The pharmaceutically acceptable carrier useful herein may comprise more than one ingredient, such as, for example, a buffer, a viscosity regulating vehicle, a surfactant, dyes, a permeation enhancer, proteinase inhibitors, or other formulation ingredients and additives, as are known in the art. The carrier may contain more than one active agent. The active agent formulation can erode or disintegrate and can be in the form of a wax formulation, solid core or tablet, for example. The formulation can immediately dissolve upon exposure to fluid or it may erode slowly with or without the presence of excipients for controlling erosion.

The active agent formulation can be designed in a multitude of ways to provide a specific drug delivery profile. One embodiment may comprise a formulation that contains a biologically acceptable solid surfactant which is capable of slow dispersion in the environmental fluid. In another embodiment, the formulation may contain a fluid-insoluble wax and a surfactant so that the formulation is susceptable to erosion in the environment. In still another embodiment, the formulation may be effervescent and provide drug delivery in a finely dispersed form. This is accomplished by the addition of a solid basic compound capable of evolving carbon dioxide in the presence of an acid in the environment of use. Suitable basic compounds are disclosed in U.S. Pat. No. 4,265,874. In a further embodiment, the formulation may include an osmotic agent or solute, such as those described above with reference to the expansion means 22, so that when the formulation comes into contact with the environmental fluid, it immediately dissolves. In yet another embodiment, the agent formulation can be comprised of an agent and a thermoresponsive composition. In this manner, the formulation would exhibit solid-like properties at room temperature of 21° C. and within a few degrees Celsius thereof, and would have a melting point that approximates mammalian body temperatures of 37° C. and within a few degrees Celsius thereof. The term "thermoresponsive" as used herein in a preferred embodiment denotes the physical-chemical property of an agent carrier composition to exhibit solid, or solid-like properties at temperatures up to 31° C and become fluid, semisolid or viscous when disturbed by heat at temperatures from 31° C., usually in the range of 31° C. to 45° C. Suitable materials useful as active agent carriers and excipients are known in the art and are disclosed in U.S. Pat. Nos. 4,595,583 and 4,874,388, for example.

The terms "active agent" and "drug" are used interchangeably herein and refer to an agent, drug, compound, composition of matter or mixture thereof which provides some therapeutic, often beneficial, effect. This includes pesticides, herbicides, germicides, biocides, algicides, rodenticides, fungicides, insecticides, antioxidants, plant growth promoters, plant growth inhibitors, preservatives, antipreservatives, disinfectants, sterilization agents, catalysts, chemical reactants, fermentation agents, foods, food supplements, nutrients, cosmetics, drugs, vitamins, sex sterilants, fertility inhibitors, fertility promoters, microorganism attenuators and other agents that benefit the environment of use. As used herein, the terms further include any physiologically or pharmacologically active substance that produces a localized or systemic effect or effects in animals, including warm blooded mammals, humans and primates; avians; domestic household or farm animals such as cats, dogs, sheep, goats, cattle, horses and pigs; laboratory animals such as mice, rats and guinea pigs; fish; reptiles; zoo and wild animals; and the like. The active drug that can be delivered includes inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autocoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, hypnotics and sedatives, psychic energizers, tranquilizers, anticonvulsants, muscle relaxants, antiparkinson agents, analgesics, antiinflammatories, local anesthetics, muscle contractants, antimicrobials, antimalarials, hormonal agents including contraceptives, sympathomimetrics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

Examples of beneficial agents which this invention can be utilized with are prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproteronol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindone, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, pednisolone, 17-β-hydroxyprogesterone acetate, 19-norprogesterone, norgestrel, norethindrone, norethisterone, norethiederone, progesterone, norgesterone, norethynodrel, ST-1435, gestodene, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinolpril, enalapril, enalaprilat, captopril, ramipril, endlapriat, famotidine, nizatidine, sucralfate, etintidine, tetratolol, minoxidil, chlordiazepoxide, diazepam, amitriptylin, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hoemone, follicle stimulating hormone, chorionic gonadotropin, gonadotropin releasing hormone, bovine somatotropin, porcine somatotropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

It is to be understood that more than one active agent may be incorporated into the active agent formulation in a device of this invention, and that the use of the term "agent" or "drug" in no way excludes the use of two or more such agents or drugs.

The agents can be in a wide variety of chemical and physical forms, such as uncharged molecules, components of molecular complexes or nonirritating, pharmacologically acceptable salts. Also, simple derivatives of the agents (such as ethers, esters, amides, etc.) which are easily hydrolyzed by body pH, enzymes, etc., can be employed.

The amount of active agent employed in the delivery device will be that amount necessary to deliver a therapeutically effective amount of the agent to achieve the desired result at the site of delivery. In practice, this will vary widely depending upon the particular agent, the site of delivery, the severity of the condition, and the desired therapeutic effect. Thus, it is not practical to define a particular range for the therapeutically effective amount of active agent incorporated into the device.

For proper delivery of the active agent, it may be desirable in some instances for the dispensing device to deliver active agent to a particular environment of use. Thus, it may be necessary for the device to remain in a particular environment of use until such time as the agent formulation has been delivered or, alternatively, for the device to pass through one particular environment to another prior to delivering agent formulation. In such cases, additional elements are included in the device, or the device is designed in such a way to provide for such particular delivery. For example, when the environment of use is the rumen of a ruminant animal, a density element may be included in the dispensing device so that the device is weighted to remain within the rumen during the dispensing period. Density elements are known in the art and are discussed in, for example, U.S. Pat. No. 4,874,388. When the environment of use is the human stomach, it may be desirable for the device to, for example, have a low initial density or to include air in that portion of the internal compartment of the device that also contains the agent formulation. In this manner, the device will float on the surface of the stomach contents and remain in the stomach until the device opens to release the formulation. Where it is desirable, on the other hand, to delay the release of an active agent which, for example, is inactivated by the stomach contents or may cause nausea or bleeding by irritating the gastric mucosa so that delivery in the stomach is not desired, an enteric coating can be applied over at least that portion of the housing of the dispensing device that is comprised of a semipermeable membrane. Enteric coatings will remain intact in the stomach but will rapidly dissolve once they arrive at the small intestine, thereafter allowing fluid to be imbibed to activate the dispensing device. Enteric coatings are well known in the art and are discussed at, for example, "Remington's Pharmaceutical Sciences", Mack Publishing Co., Easton, Pa.

The total delay time prior to separation of the dispensing device and delivery of the active agent formulation can be controlled by a number of means. The effects of the design and placement of the openings in the first wall section of the device have been discussed previously herein. Additionally, for example, the rate of fluid imbibition into the expansion means can be controlled by the particular choice of semipermeable membrane. The rate of expansion of the expansion means can be controlled by the choice of composition of the expansion means. The distance of overlap between the open end portions of the first and second wall sections can determine the period of time required for the two sections to separate. Combinations. of such means may be used. Such control means are known in the art and can be determined without undue experimentation.

The devices of the present invention may be prepared by methods known in the art. For example, the first and second wall sections may be prepared by injection-molding or extrusion, for example, of the appropriate wall-forming materials into the desired shapes. Alternatively, one or both of the sections may be prepared by coating a substrate, such as a gelatin capsule or a portion thereof, with the wall-forming materials. The openings in the side wall of the first wall section may be formed during manufacture of the wall section, as by injection-molding or extrusion, or they may be formed after manufacture, by laser-drilling, cutting, punching, and the like. The osmotic expansion means may be separately prepared as a tablet and the tablet placed into the second wall section at the time of assembly of the device, or the osmotic material as particles, granules and the like may be pressed into the second wall section.

The device may be assembled in any number of ways, as can be determined without undue experimentation. For example, the first and second wall sections are formed to the desired shapes, after which the osmotic expansion means is placed in the bottom of the second wall section and a partition layer or push plate, if included, is placed above the expansion means. The active agent formulation is placed into the first wall section, and the open end of the first wall section is then positioned inside the open end of the second wall section and the two sections are compressed until they fit together tightly.

The above description has been given for ease of understanding only. No unnecessary limitations should be understood therefrom, as modifications will be obvious to those skilled in the art.

What is claimed is:

1. A fluid-imbibing delivery device for dispensing an active agent to a fluid environment of use for an extended period of time following an initial delayed startup of delivery, wherein the device comprises:
    a) a housing comprising a first wall section and a second wall section in reversibly sliding telescopic arrangement with each other, the first wall section having an open end adapted to fit within the second wall section and the second wall section comprising in at least a portion a semipermeable composition, which housing maintains its integrity in the environment of use;
    b) an internal compartment surrounded and defined by the first and second wall sections of the housing;
    c) at least one active agent formulation comprising a drug in a portion of the compartment defined by the first wall section;
    d) at least one opening in the side wall of the first wall section, each opening extending longitudinally along a portion of the side wall of the first wall section and beinq covered by said second wall section prior to exposure to the environment of use, for releasing the active agent formulation comprising the drug followinfi separation of the first and second wall sections upon exposure to the environment of use; and
    e) expansion means comprising an osmopolymer in a portion of the compartment defined by the second wall section, for separating apart the first and second wall sections of the housing after exposure to the environment of use.

2. A delivery device according to claim 1 wherein there are two to ten openings in the side wall of the first wall section.

3. A delivery device according to claim 1 wherein the first wall section is comprised of a substantially impermeable composition.

4. A dispensing device according to claim 1 wherein the active agent formulation comprises a liquid, a solid, a semisolid, a thermoresponsive composition, or a plurality of dosage forms.

5. A dispensing device according to claim 1 which further comprises a push plate between the expansion means and the open end of the first wall section.

6. A method for delivering an active agent comprising a drug to a fluid environment of use for an extended period of time following an initial delayed startup of delivery, wherein the device comprises:
    1) placing a delivery device into the environment of use, the dispensing device comprising:
        a) a housing comprising a first wall section and a second wall section in reversibly sliding telescopic arrangement with each other, the first wall section having an open end adapted to fit within the second wall section and the second wall section comprising in at least a portion a semipermeable composition, which housing maintains its integrity in the environment of use;
        b) an internal compartment surrounded and defined by the first and second wall sections of the housing;
        c) at least one active agent formulation comprising a drug in a portion of the compartment defined by the first wall section;
        d) at least one opening in the side wall of the first wall section, each opening extending longitudinally along a portion of the side wall of the first wall section and beinq covered by said second wall section prior to exposure to the environment of use, for releasing the active agent formulation comprising the drug followinq separation of the first and second wall sections upon exposure to the environment of use; and
        e) expansion means comprising an osmopolymer in a portion of the compartment defined by the second wall section, for separating apart the first and second wall sections of the housing after exposure to the environment of use;
    2) allowing fluid to be imbibed through at least a portion of the second wall section of the housing of the dispensing device for causing the expansion means to expand and exert pressure on the slidably connected first and second wall sections to push apart and separate the first and second wall sections to deliver the active agent formulation comprising the drug through the at least one opening in the side wall of the first wall section to the environment over an extended period of time after an initially delayed period of time.

7. A method according to claim 6 wherein there are two to ten openings in the side wall of the first wall section.

8. A method according to claim 6 wherein the first wall section is comprised of a substantially impermeable composition.

9. A method according to claim 6 wherein the active agent formulation comprises a liquid, a solid, a semisolid, a thermoresponsive composition, or a plurality of dosage forms.

10. A method according to claim 6 which further comprises a push plate between the expansion means and the open end of the first wall section.

* * * * *